(12) United States Patent
von Schuckmann (10) Patent No.: US 8,327,842 B2
(45) Date of Patent: Dec. 11, 2012

(54) INHALER FOR POWDERED, PARTICULARLY MEDICAL SUBSTANCES

(75) Inventor: Alfred von Schuckmann, Kevelaer (DE)

(73) Assignee: Sanofi SA, Meyrin (CH)

( * ) Notice: Subject to any disclaimer, the term of this patent is extended or adjusted under 35 U.S.C. 154(b) by 1415 days.

(21) Appl. No.: 11/660,887

(22) PCT Filed: Aug. 19, 2005

(86) PCT No.: PCT/EP2005/054094
§ 371 (c)(1), (2), (4) Date: Feb. 23, 2007

(87) PCT Pub. No.: WO2006/021546
PCT Pub. Date: Mar. 2, 2006

(65) Prior Publication Data
US 2007/0289593 A1 Dec. 20, 2007

(30) Foreign Application Priority Data
Aug. 27, 2004 (DE) .......................... 10 2004 041 524

(51) Int. Cl.
*A61M 16/00* (2006.01)
*A61M 15/00* (2006.01)
*B05D 7/14* (2006.01)
*B65D 83/06* (2006.01)

(52) U.S. Cl. .......... 128/203.15; 128/203.12; 128/203.13

(58) Field of Classification Search ............. 128/203.15, 128/203.12, 205.24, 203.19, 203.21, 200.11, 128/200.12, 200.14, 200.21, 200.23, 200.24, 128/203.13, 203.14, 203.16, 203.22, 203.23; 222/630, 636, 366, 344, 361, 367, 425, 452
See application file for complete search history.

(56) References Cited

U.S. PATENT DOCUMENTS

| 2,029,835 | A | * | 2/1936 | Reichle ..................... 401/266 |
| 4,095,596 | A | | 6/1978 | Grayson |
| 4,117,946 | A | | 10/1978 | Kessler |
| 5,239,992 | A | * | 8/1993 | Bougamont et al. ...... 128/203.15 |
| 5,429,122 | A | | 7/1995 | Zanen et al. |
| 5,435,301 | A | * | 7/1995 | Herold et al. ............ 128/203.15 |
| 5,505,196 | A | | 4/1996 | Herold et al. |

(Continued)

FOREIGN PATENT DOCUMENTS
DE 100 47 722 A 4/2002
(Continued)

OTHER PUBLICATIONS
International Search Report.

*Primary Examiner* — Justine Yu
*Assistant Examiner* — Colin W Stuart
(74) *Attorney, Agent, or Firm* — McDonnell Boehnen Hulbert & Berghoff LLP (57) ABSTRACT

The invention relates to an inhaler for powdered, particularly medical substances, including a suction air duct that extends to a mouthpiece, a reservoir for the substance, and an at least linearly movable dosing chamber for separating a specific amount of the substance from the reservoir and placing the amount into a transfer position in order for the same to be transferred to the suction air flow. In order to further develop a generic inhaler in an advantageous manner, especially so as to charge the dosing chamber by separating a specific amount of substance from the reservoir, the dosing chamber can be rotationally moved in a superimposed fashion while being arranged eccentric to a corresponding axis of rotation.

7 Claims, 6 Drawing Sheets

U.S. PATENT DOCUMENTS

| | | | |
|---|---|---|---|
| 5,524,613 A * | 6/1996 | Haber et al. ............. 128/203.15 |
| 5,628,307 A | 5/1997 | Clark et al. |
| 5,765,552 A * | 6/1998 | Zanen et al. ............. 128/203.15 |
| 6,119,688 A | 9/2000 | Whaley et al. |
| 6,371,111 B1 * | 4/2002 | Ohki et al. ............... 128/203.15 |
| 6,488,648 B1 * | 12/2002 | Matsugi et al. ................. 604/57 |
| 2003/0136405 A1 | 7/2003 | Goede et al. |
| 2004/0035421 A1 | 2/2004 | Schuckmann |
| 2004/0187868 A1 * | 9/2004 | Hochrainer et al. ..... 128/203.15 |
| 2007/0289593 A1 | 12/2007 | Von Schuckmann |
| 2010/0300441 A1 | 12/2010 | Von Schuckmann |
| 2010/0309020 A1 | 12/2010 | Von Schuckmann |

FOREIGN PATENT DOCUMENTS

| | | |
|---|---|---|
| DE | 101 06 788 A1 | 8/2002 |
| DE | 101 44 572 A1 | 3/2003 |
| RU | 2138303 C1 | 9/1999 |
| WO | WO 00/64518 A | 11/2000 |
| WO | 0226299 A1 | 4/2002 |
| WO | 2004/033009 | 4/2004 |

\* cited by examiner

INHALER FOR POWDERED, PARTICULARLY MEDICAL SUBSTANCES

CROSS REFERENCE TO RELATED APPLICATIONS

Applicant claims priority under 35 U.S.C. §119 of German Application No. 102004041524.2 filed Aug. 27, 2004. Applicant also claims priority under 35 U.S.C. §365 of PCT/EP2005/054094 filed Aug. 19, 2005. The international application under PCT article 21(2) was not published in English.

The invention relates to an inhaler for powdered, particularly medical substances, with a suction air channel leading to a mouthpiece, also a storage chamber for the substance and a linearly moved dosing chamber for apportioning a specific amount of substance from the storage chamber and bringing the amount of substance into a transfer position, for transfer to the suction air stream.

An inhaler of the type in question is known from DE 10 144 572 A1. The content of this patent application is hereby incorporated in full in the disclosure of the present invention, including for the purpose of incorporating features of this application in claims of the present invention.

It is an object of the invention to develop an inhaler of the generic type in an advantageous way, in particular with regard to the charging of the dosing chamber by apportioning a specific amount of substance from the storage chamber.

This object is achieved first and foremost by the subject matter of claim 1, it being provided that the dosing chamber is rotationally moved in a superposed manner and is disposed eccentrically in relation to a corresponding axis of rotation. As a result of such a configuration, a structurally simple, functionally reliable inhaler is achieved, the dosing chamber of which is filled in a simple and reliable way by the rotational movement superposed on the linear movement. This is further assisted by the dosing chamber, in the course of the rotational movement with a radial spacing around the axis of rotation, being moved by the substance stored in the storage chamber to discharge in an apportioned manner a predetermined amount of substance. Discharge of a constantly equal, predefined amount of substance in an apportioned manner from the storage chamber is correspondingly effected. Once the dosing chamber has been displaced in a helical manner into the transfer position, said storage chamber is ready for the transfer to the suction air stream and the accompanying inhalation.

The subject matters of the further claims are explained below with reference to the subject matter of Claim 1, but may also be of importance in their independent formulation. For instance, it is further proposed that the dosing chamber is formed in a plunger slide fashioned as a flat part. More preferably, the dosing chamber is configured here as a transverse bore in the plunger slide fashioned as a flat part. It has proven to be particularly advantageous here if, as further preferred, the plunger slide is displaceable in a manner dependent on the closure cap, so that handling in the customary way to achieve closing and opening by turning the closure cap at the same time achieves charging of the dosing chamber and a linear, superposed rotational movement of the dosing chamber into the transfer position. A particularly effective measure is obtained by a conical transverse bore to form the dosing chamber. The flat part forming the plunger slide has in cross-section an edge ratio of approximately 1:2 to 1:5. The end of this flat part that is free in the plunging direction may for example be pointed in the manner of a screwdriver blade. The fashioning of the plunger slide in the manner of a flat part achieves the effect of a rotationally loosening action in the central region of the substance stored in the storage chamber, which at the same time is conducive to the plunging of the plunger slide into the mass of powder. To stop the amount of substance that is discharged in an apportioned manner from falling out of the dosing chamber in the transfer position before it is transferred to the suction air stream, it is provided in a development of the subject matter of the invention that the plunger slide interacts outside the storage chamber with a closure plunger that is movable in relation to the plunger slide. This closure plunger is preferably linearly movable in relation to the plunger slide and is correspondingly passed through by the plunger slide fashioned as a flat part, which is a further reason for the closure plunger and the plunger slide to be disposed such that they do not rotate in relation to each other. For the transfer of the amount of substance to the suction air stream, the closure plunger must correspondingly first be displaced into a position releasing the dosing chamber for substance discharge. This is preferably performed by the closure plunger being movable into a release position with respect to the dosing chamber in dependence on a reduced suction pressure. The necessary reduced suction pressure is applied in the course of the inhalation. For this purpose, the patient places his lips around the mouthpiece of the inhaler in a manner familiar to him, in order to achieve a suction air stream in the suction air channel by inhaling. The reduced suction pressure that is automatically built up hereby is sufficient for displacing the closure plunger into the release position and subsequently clearing out the dosing chamber, and for the accompanying transfer of the amount of substance to the suction air stream. The way in which the closure plunger is disposed ensures that the partial amount discharged in an apportioned manner is supplied in the dosing chamber up until inhalation, i.e. up until transfer to the suction air stream. The release or opening of the dosing chamber takes place automatically in the course of customary handling. To further improve the distribution of the powdered substance or the apportioned amount of substance in the suction air, the so-called dispersing region, downstream of the transfer region in the direction of flow, is further formed in an advantageous way to the extent that the suction air channel has a radially outward deflection above the dosing chamber. Accordingly, before the amount of substance transferred to the suction air stream leaves, it also undergoes a deflection, this radially outward deflection also leading into an outlet portion in the region of the mouthpiece that is similar to an annular space. Correspondingly, the substance leaves in the form of a circular ring if the mouthpiece is viewed looking down on top of it. It is also proposed that the plunger slide itself forms part of the flow deflection, for instance in particular such that, in an end region facing away from the flat part having the dosing chamber and correspondingly facing toward the mouthpiece, it takes the form of a disk of a circularly round outline, which offers the radially outward deflection of the suction air channel in the transfer position.

The invention is explained in more detail below with reference to the accompanying drawings, which merely represent an exemplary embodiment and in which.

Shown and described is an inhaler 1, which is realized as a conveniently portable pocket device in the form of a short stick, with a shape-determining stepped, cylindrical housing 2.

The cylindrical housing 2, which is like a small tube, passes at the top end of the inhaler 1 into an attached mouthpiece 3, which is flattened appropriately for a mouth and can be protectively engaged over by means of a cup-shaped closure cap 4. The latter is realized as a screw cap, for which purpose an internal thread 5 associated with it engages in a corresponding external thread 6 on the lateral wall of the housing 2. In the region where the mouthpiece 3 is attached, a clip 7 is integrally formed on the outer sleeve wall of the closure cap 4.

At the bottom end, the end edge of the cup-shaped closure cap 4 butts with a stop-limiting and sealing effect against an annular shoulder 8, which is achieved on account of the aforementioned step of the cylindrical housing 2.

The closure cap 4 serves at the same time as an actuating handle 9 for delivering a powdered substance 10 in reproducible portions 10', for which purpose the axial screw stroke of the engagement of the threads 5/6 is used. The substance 10 is accommodated in a storage chamber 11 of the housing 2 in an optionally refillable manner. The dosing device, transporting in each case a portion 10' to a transfer point U lying outside the storage chamber 11, is designated as a whole by D.

With respect to the material that can be dosed, it is a medical, powdered substance 10. For example, basic substances capable of being transported by suction stream, such as lactose, may act as a carrier for micronized fine particles of medicament sticking to the surface.

Provided downstream of the dosing device D is a so-called dispersing region, in which the user produces a suction air stream S. This completely carries away the exactly apportioned amount 10' of the substance 10 at the transfer point U. The suction air channel leading to the mouthpiece 3 is provided with the reference numeral 12.

The lower termination of the storage chamber 11 is formed by a cup-shaped pressure-exerting base 13, which is under spring loading in the direction of the mouthpiece 3 by means of a compression spring 14. The compression spring 14 is supported by the bottom end turn on a base cap 15 closing the housing 2 there. Said base cap is in latching engagement with the portion of the housing 2, which is here of larger cross-section, a corresponding latching collar 16 of the base cap 15 engaging in a matching annular groove of the housing 2.

The top end turn of the prestressed compression spring 14 acts in loading manner on an inner shoulder 17 of a hollow piston 18 of the piston-shaped device 13/18. As can be gathered from the illustrations, the stepped cup-shaped pressure-exerting base 13 is connected in a latching manner to the inner shoulder 17 of the hollow piston 18.

The cup edge of the pressure-exerting base 13 provides an annular lip 19, which on account of its rubber-elastic material wipes off the wall of the storage chamber 11 without any substance being lost.

A hollow standing spigot 20 extends centrally from the base cap 15. Together with the hollow piston 18 surrounding it at a spacing, said standing spigot forms a spring chamber 21 for the compression spring 14.

At the mouthpiece end, the storage chamber 11 terminates with a cup-shaped rotary part 22, which forms by its cup base the top 23 of the storage chamber 11 engaging over the housing 2.

A guiding opening 24 is left at the center of the top 23. This indirectly or directly formed guiding opening 24 receives a plunger slide 25, as the key component of the dosing device D. As a result of being appropriately configured, said plunger slide acts as a moving dosing chamber 26 for the portion 10' to be lifted out, the movement of the plunger slide 25 taking place linearly in the longitudinal center axis x-x of the substantially rotationally symmetrically configured inhaler 1, overlaid by a rotational movement carried out about this longitudinal center axis x-x. The plunger slide 25 is fashioned substantially as a flat part with an elongate rectangular cross-section. The length ratio of the narrow side to the wide side in the exemplary embodiment represented is approximately 1:3.

At the end remote from the mouthpiece 3, the plunger slide 25 forms a point similar to a screwdriver blade. The two mirror-symmetrical oblique flanks extend here from the respective wide sides of the plunger slide 25. The free end, provided with the oblique flanks, is blunted.

On account of the co-rotation of the plunger slide 25, the cross-sectional configuration of the plunger slide 25 and the pointing of the free end region have a loosening effect in the central region with respect to the mass of powdered substance 10.

The stroke of the dosing chamber 26, moving in a linear manner with superposed rotational movement, makes allowance in both end positions of the plunger slide 25 for the cross-section of the guiding opening 24 to be kept closed with a doctor-blade or wiping-off effect, filling the dosing chamber, over the length of said opening 24.

The end of the closure cap 4 for the mouthpiece forms a docking point 28 between plunger slide 25 and closure cap 4 that unlatches when overloaded. The latching means on the closure cap is in this case a ring of hooks capable of resilient deflection. The corresponding end of the plunger slide 25 is fashioned in a rotationally symmetrical manner in cross-section, a disk-shaped radial collar 29 also emerging in the transitional region from the flat part portion to the cylindrical end portion. With an axial spacing in relation to this radial collar 29, the end region of the plunger slide 25 that is facing away from the flat part fashions a latching head 30. Between said latching head and the radial collar 29 there is formed a narrow waist-like annular groove 31. Inwardly directed lugs 32 of the resilient tongues of the ring of hooks engage in said annular groove. The latching head 30 can be overcome in both directions by the lugs 32.

The lugs 29, or their resilient tongues, are realized on a small tube 33 which protrudes into a central mouthpiece opening 3' and extends from the inner side of the top of the closure cap 4, at which it is rooted.

The mouthpiece 3 acts via a lateral wall 34 in an anchoring manner on the neck of the housing 2. With reference to the illustrations, this anchorage is formed underneath the top 23 of the rotary part in the form of a latching point 35 between the two parts 2, 3. It may be an irreversible latching point 35. In addition, the top 23 of the rotary part 22 is engaged over in a supported manner by an annular shoulder 36 of the lateral wall 34.

The central opening 3' of the mouthpiece 3 is formed in the region of a cup-shaped dispersing part 37, disposed substantially in an inverted position. This is accomplished by passing centrally through the base 38 of the dispersing part. The dispersing part 37, opening in the direction of the rotary part 22, has a cup wall 39, with an outside diameter which corresponds to the outside diameter of the cup wall 40 of the rotary part 22. The cup-shaped rotary part 22 and the cup-shaped dispersing part 37 face each other with their openings, the dispersing part 37 being supported with its free annular edge on the associated annular edge of the cup wall 40 of the rotary part.

Both cup walls 39 and 40 are spaced radially inward in relation to the inner wall of the lateral wall 34. Correspondingly, an annular space 41 is respectively obtained around the rotary part 22 and around the dispersing part 37.

The inside diameter of the cup wall 39 of the dispersing part 37 is adapted to the outside diameter of the disk-like radial collar 29 of the plunger slide 25. The latter correspondingly undergoes guidance in a linear direction in the cup-like dispersing part 37.

Respectively toward their open end regions, the cup spaces both of the rotary part 22 and of the dispersing part 37 widen radially outward, with the material of the respective cup walls 39 and 40 being reduced. As a result of this configuration, a radially widened overflow region 42 is obtained.

Spaced away from the cup base 38 of the dispersing part 37 by approximately the material thickness of the radial collar 29 of the plunger slide 25, radial passages 43 are provided in the cup wall 39, for connecting the space inside the cup with the peripheral annular space 41. As shown, two diametrically opposed passages 43 may be provided. Alternatively, one peripheral passage, interrupted by supporting webs, may also be provided.

The annular discharge space 44, surrounding the cup base 38 of the dispersing part 37, is separated from the annular space 41 extending approximately as an axial extension by a sealing collar 45, which protrudes radially outward on the cup wall 39, which sealing collar 45 is supported on the inside of the lateral wall 34. As a result of this configuration, a defined deflection of the suction air channel 12 is achieved, from the central axial alignment radially outward into the substantially axially aligned annular outlet space 44.

The axial lengths of the rotary part 22 and the dispersing part 37 in the region of their cup walls 39 and 40 are chosen such that the powder-drawing plunging stroke of the plunger slide 25 out of a filling plane in the storage chamber 11 to the transfer point U above the top 23 is ensured.

The defined ready-to-empty position of the dosing chamber 26 is obtained by an extension limiting stop of the plunger slide 25 in the region of its radial collar 29 against the cup base 38 of the dispersing part 37.

The dosing chamber 26 is realized as a transverse bore running substantially perpendicularly in relation to the longitudinal center axis x-x.

Figure 1:
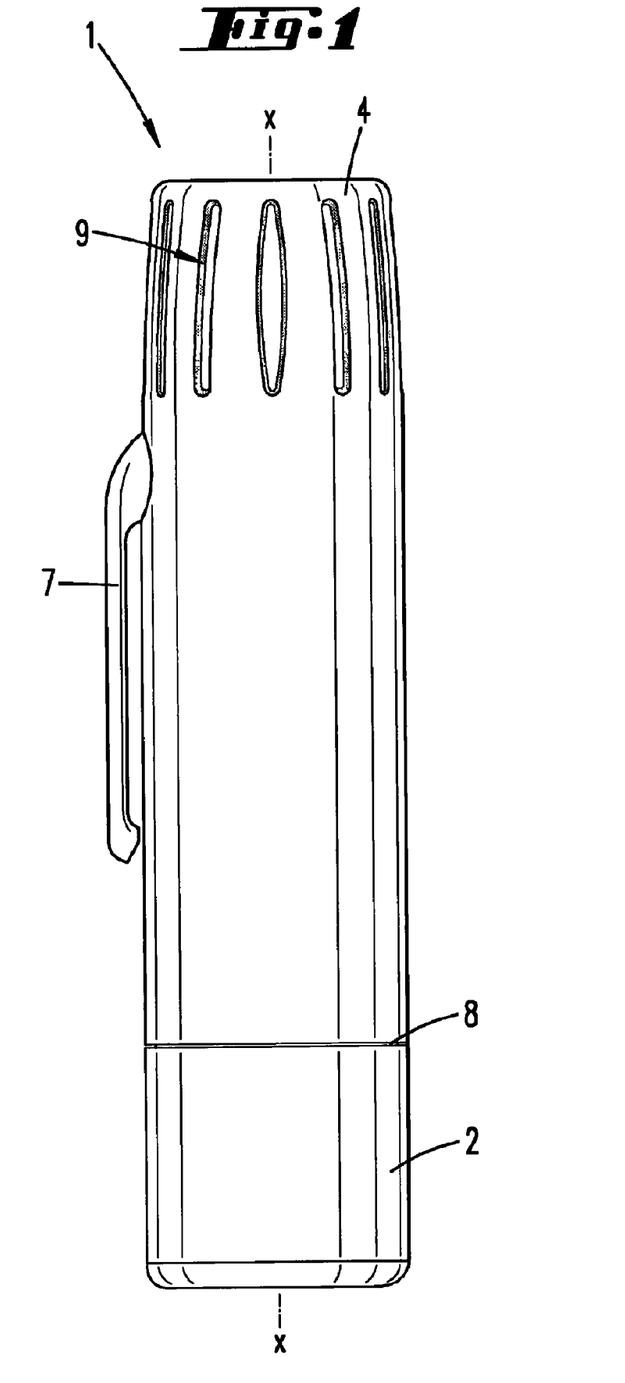
FIG. 1 shows the inhaler according to the invention in side view, enlarged, in the basic position with the cap closed.
Figure 2:
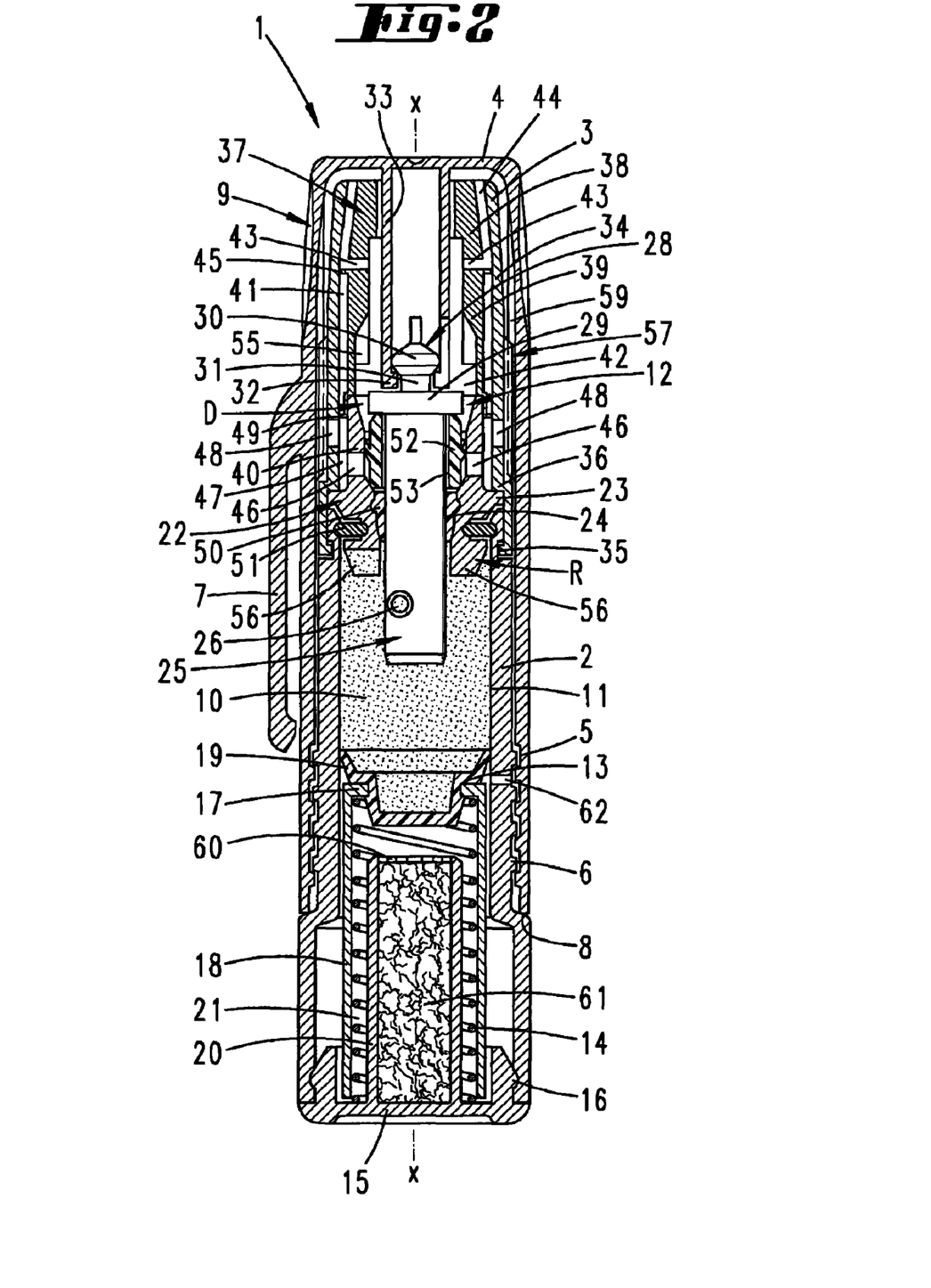
FIG. 2 shows the vertical section of this.
Figure 3:
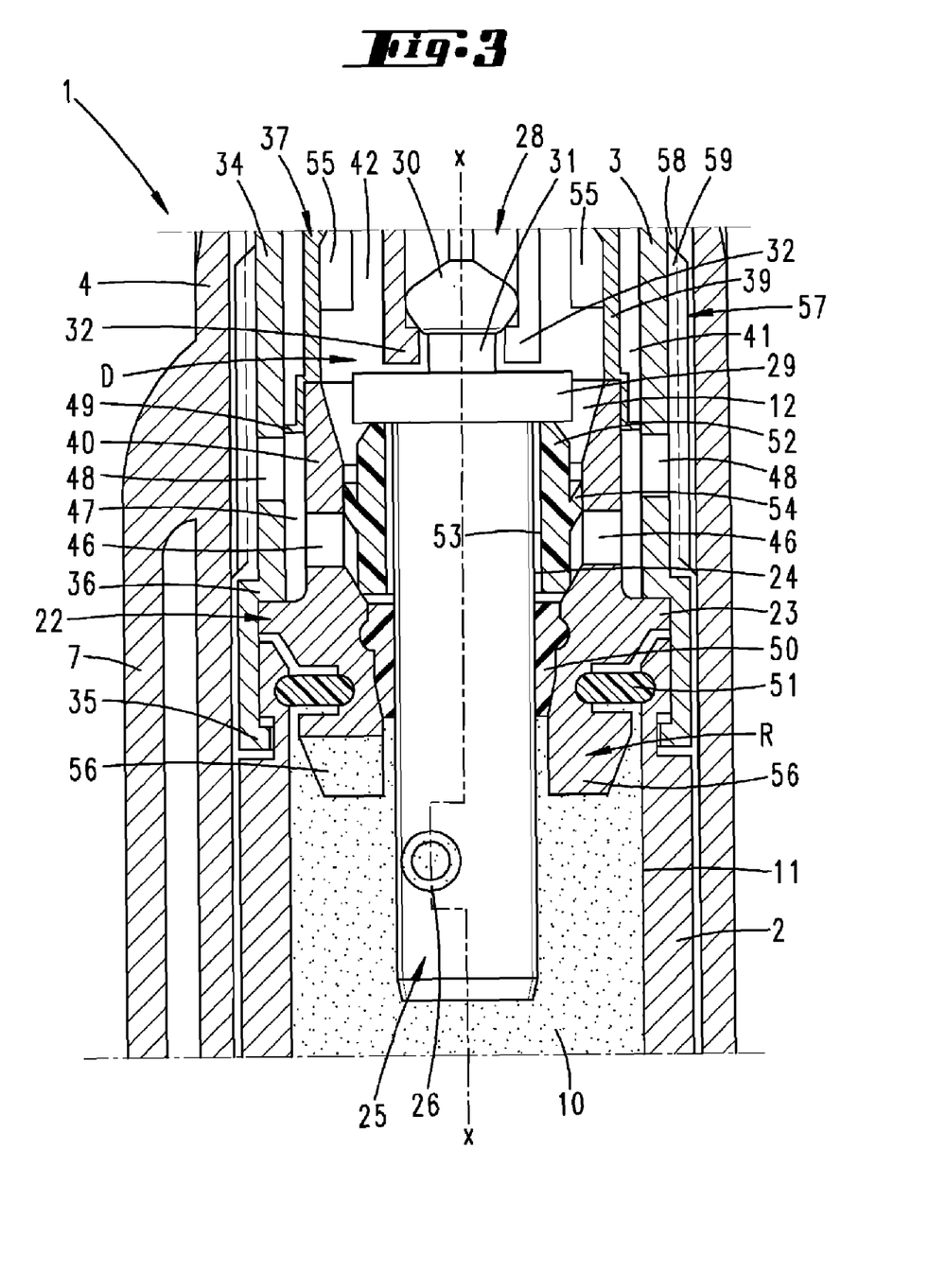
FIG. 3 shows an enlargement taken from FIG. 2, for the region of a dosing device.

This longitudinal center axis x-x at the same time forms the axis of rotation. The dosing chamber 26 is eccentrically disposed with respect to this axis of rotation, so furthermore passes through the wide sides of the plunger slide 25 fashioned as a flat part. As can be gathered in particular from the illustration in FIG. 2, the dosing chamber 26 is disposed such that it is associated with a side edge of the wide surface, at a spacing from the free end of the plunger slide 25.

Figure 4:
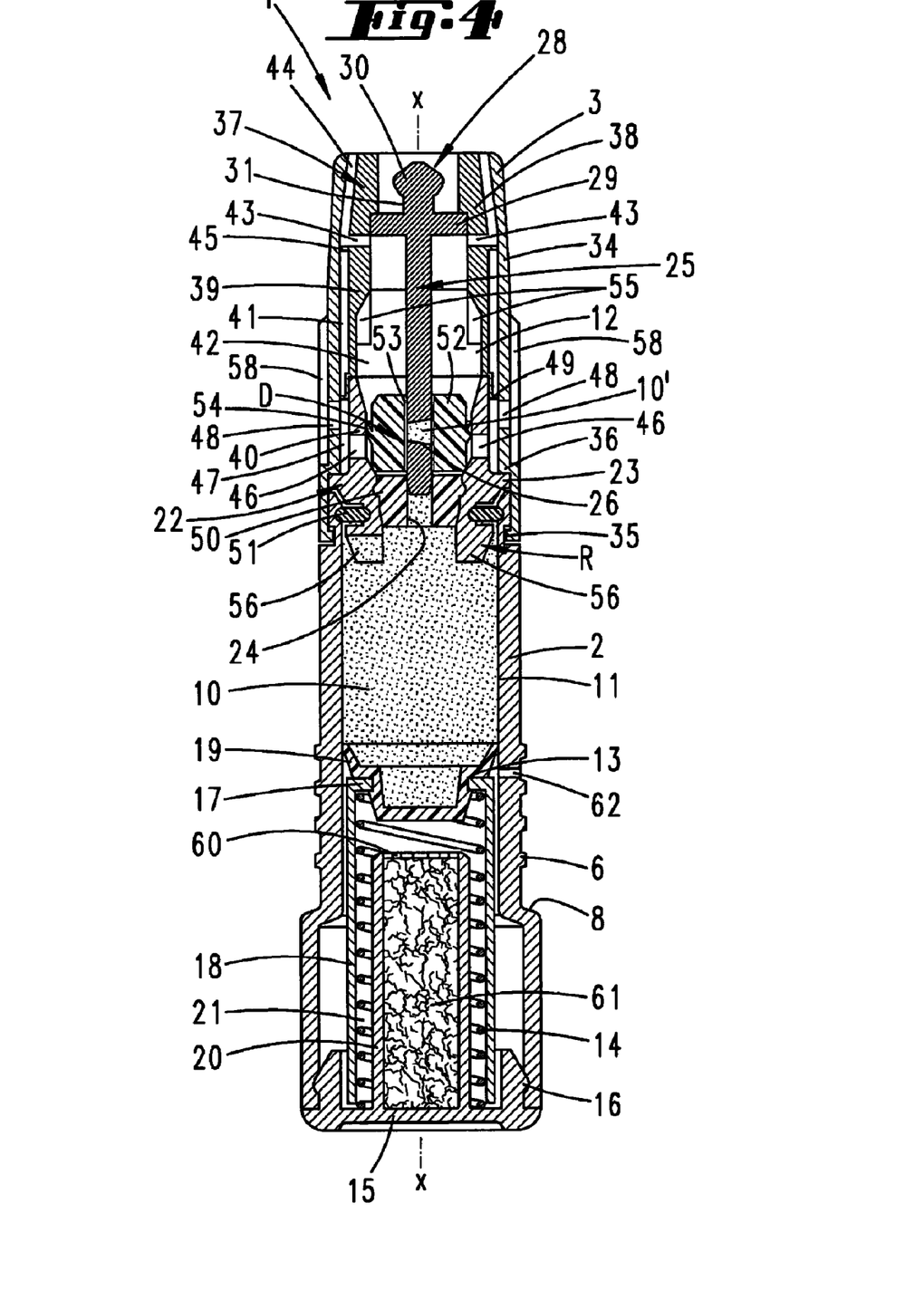
FIG. 4 shows a sectional representation according to FIG. 2 along the line x-x of FIG. 3, with the closure cap removed and resultant displacement of the dosing chamber into the ready-to-remove position.

In the ready-to-empty position according to FIG. 4, the dosing chamber 26 is in the active region of the central suction air stream S. An air passage 46 connecting with the suction air channel 12 and formed in the cup wall 40 of the rotary part 22 is associated with the dosing chamber 26. Said air passage comprises radial bores which extend in the vicinity of the base of the cup-shaped rotary part 22 with an axial spacing above the upper side of the top 23.

Such an air passage 46 is provided upstream and at a radial spacing from both open ends of the dosing chamber 26. One precaution in this connection is that associated with the end of the dosing chamber 26 which is of larger clear diameter and is formed by a conical transverse bore is an air passage 46 of a smaller diameter than said larger-diameter end and associated with the end of the dosing chamber 26 which is of smaller clear diameter is an air passage 46 of a larger diameter than said smaller-diameter end. This way there is produced a greater reduced pressure with a predominant discharging effect with respect to the administered portion 10' downstream of the air passage 46 of smaller diameter. Nevertheless, the discharge, i.e. emptying of the dosing chamber 26, takes place from both ends. A solution in which the air passages 46 are of the same diameter is shown in the drawings.

The air passages 46, formed on the cup-shaped rotary part 22 guiding the plunger slide 25, are also in flow communication with air inlets 48 spaced radially by way of a rearward annular inflow space 47. Said air inlets are also configured as bores and represent the connection to the atmosphere. The annular inflow space 47 is fashioned between the outer side of the cup wall 40 of the cup-shaped rotary part 22 and the inner side of the lateral wall 34 of the mouthpiece 3, as an axial extension of the annular space 41 described. A stepped, radially outwardly protruding sealing collar 49 at the end facing toward the cup opening of the dispersing part 37 serves for separating the annular spaces from one another and for the radial alignment of the dispersing part 37 while supported on the inner side of the lateral wall 34. The sealing collars 49 and 45 of the dispersing part 37 prevent a flow bypass between the air inlets 48 and the annular outlet space 44 in the region of the mouthpiece 3.

The air passages 46 are disposed axially offset in relation to the air inlets 48, the latter lying closer to the mouthpiece 3. The described spatial distancing leads to an initially contracting inflow of sucked-in air following on from the main suction air stream S.

The guiding opening 24 for the plunger slide 25 is formed such that it has a wiping-off effect, as a result of which there is also no dosage-falsifying entrainment of powder material that may be sticking to the lateral surface of the plunger slide. The guiding opening 24 is not formed directly by the rotary part 22, but by a sealing bush 50 lining this passage. Said sealing bush consists of rubber-elastic material and is held by being clipped into the top 23 by latching means.

Between the rotary part 22 and the housing 2, which forms the storage chamber 11, there is likewise a sealing element. This is achieved by a sealing ring 51 of rubber-elastic material inserted between the inside wall of the storage chamber 11 and the rotary part 22. Said sealing ring is fitted under preloading in annular grooves of both parts 2, 22. Both of the peripheral annular grooves, which accommodate the sealing ring 51, have a half-round cross-sectional configuration. The corresponding regions of the sealing ring 51 are correspondingly shaped.

The sealing bush 50 is connected to the rotary part 22 in a rotationally fixed manner. The guiding opening 24 is formed in a manner adapted to the cross-sectional configuration of the plunger slide 25, likewise in an elongate rectangular fashion, and as a result of this positive engagement the plunger slide 25 is also connected to the rotary part 22 in a rotationally fixed manner.

Interacting with the plunger slide 25 is a closure plunger 52, which is movable in relation to the latter outside the storage chamber 11. Said closure plunger may consist of a rubber-elastic material and is passed through centrally by the flat portion of the plunger slide 25, for which purpose the closure plunger 52 has a matched bearing opening 53, of an elongate rectangular form in outline. This bearing opening 53 is slightly enlarged with respect to the cross-sectional dimension of the flat portion of the plunger slide 25, as a result of which a low-friction displacement of the closure plug 52 on the plunger slide 25 is achieved.

The closure plunger 52 is provided with a radially outward peripheral sealing lip 54, which in a ready-to-transfer position according to the illustration in FIG. 4 interacts with the inside wall of the cup wall 40 of the rotary part, this being above the air passages 46 with reference to the storage chamber 11.

In this ready-to-transfer position, the closure plug 52 is located in a blocking manner in the suction air channel 12, with the dosing chamber 26 that is provided with the portion 10' of the substance 10 being sealed off on both sides. If the inhaler 1 is put down after it has been activated, that is to say after the plunger slide 25 with the filled dosing chamber 26 has been displaced into the ready-to-transfer position, this does not lead to loss of the apportioned amount from the dosing chamber 26 as a result of the way in which the closure plunger 52 is disposed. The closure plug 52 is fashioned in a self-locking manner.

The displacement of the closure plunger 52 is only possible deliberately, most easily by activation of the suction air stream S, that is to say by the customary intake of inhalation. Depending on the reduced suction pressure that this produces, the closure plunger 52 is displaced axially upward along the portion comprising the flat part of the plunger slide 25, to release the dosing chamber 26 on both sides. The closure plunger 52 is hereby moved into the radially widened overflow region 42, this axial displacement being stop-limited. Serving for this purpose are axially aligned stop webs 55, which extend radially inward from the inside wall of the cup wall 39 of the dispersing part and against which the annular sealing lip 54 of the closure plunger 52 butts in a blocking manner. The radial spacing of the stop webs 55 from one another corresponds to the guiding cross-section of the dispersing part 37 and consequently to the outside diameter of the radial collar 29 on the plunger slide side.

Figure 5:
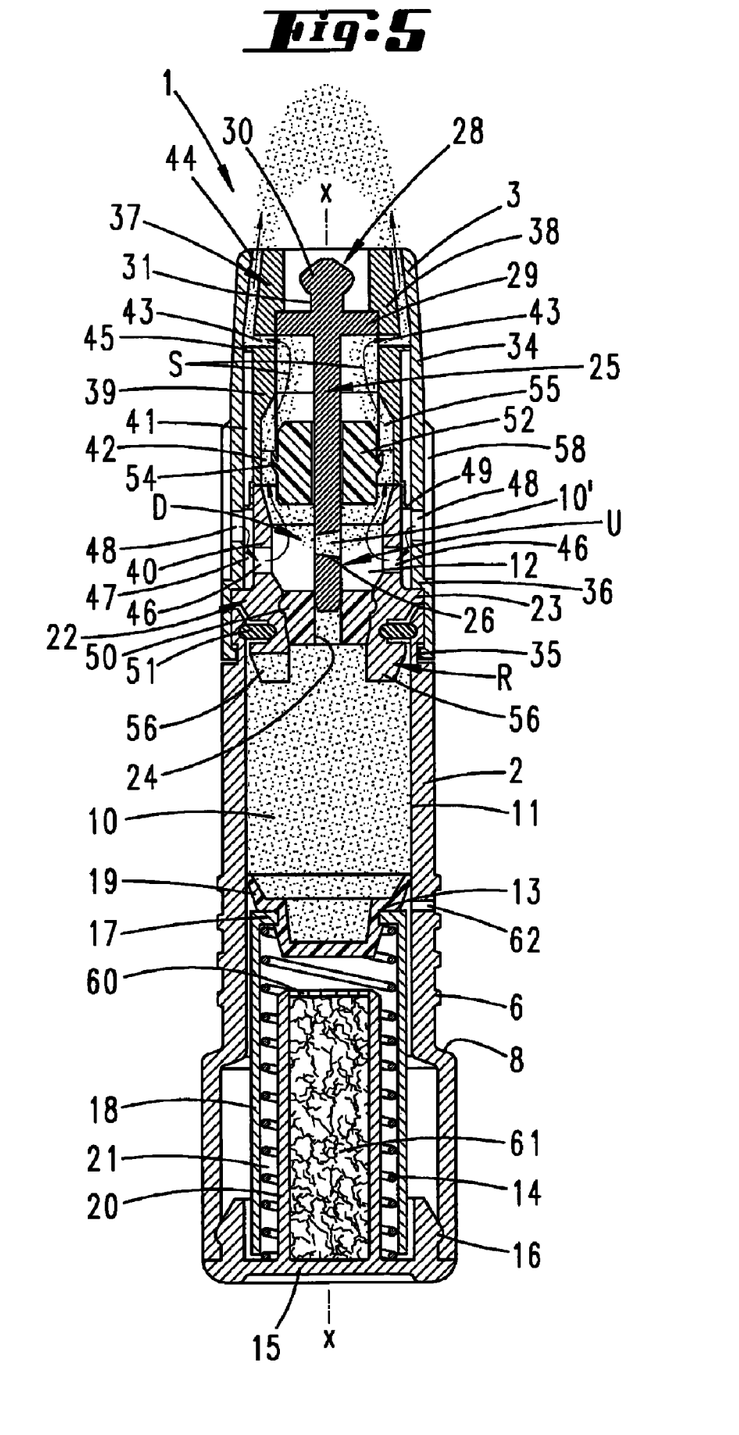
FIG. 5 shows a sectional representation corresponding to FIG. 4, but representing a position in the course of inhalation.
Figure 6:
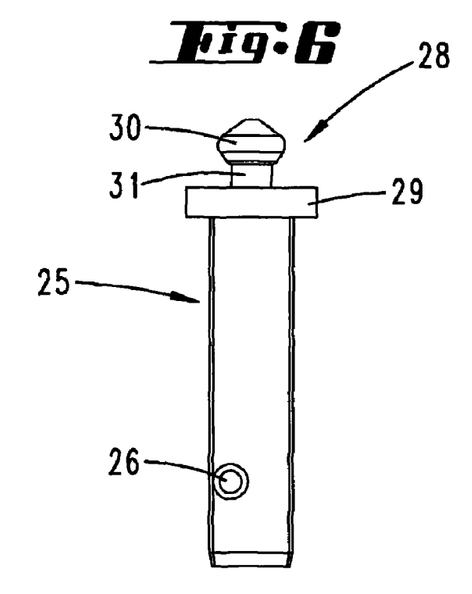
FIG. 6 shows the plunger slide having the dosing chamber on its own in elevation.
Figure 7:
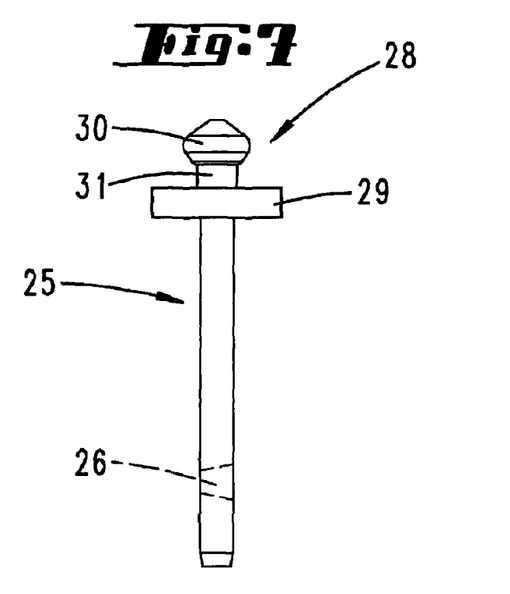
FIG. 7 shows the side view of this.
Figure 8:
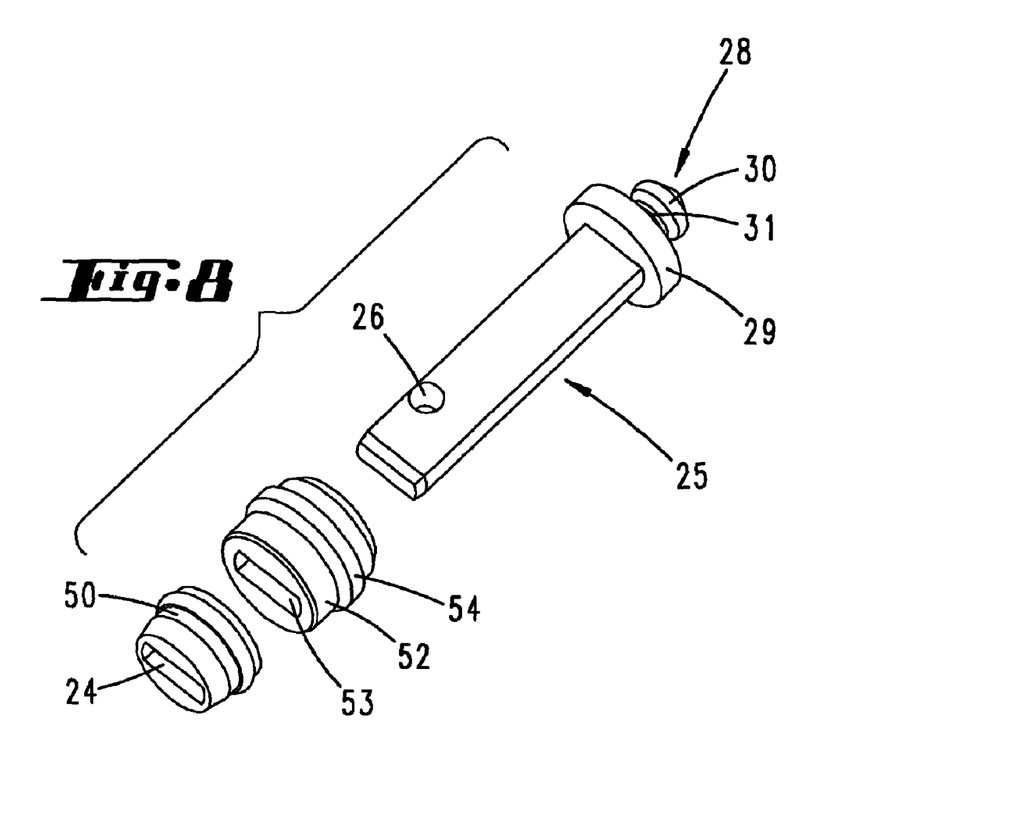
FIG. 8 shows the plunger slide in a perspective representation, with a closure plunger that can be associated with it and with a sealing bush.

In the course of the inhalation—as schematically represented in FIG. 5—flow passes around the closure plunger 52, lying in the region 42 of the mouthpiece 3.

Conducive to the emptying of the storage chamber 11 is the way in which the powdered substance 10 is kept ready in the drawing region. Conditions are created to ensure an isostructural or homogeneous filling of the dosing chamber 26, fed from a surrounding region where the substance has been loosened. The rotary part 22 is used in particular for this purpose. It has a rotor R acting in the upper region of the storage chamber 11. Using the rotation of the rotary part 22, a loosening of the stored substance is obtained. Rotor blades 56 form a scoop. In this respect, two rotor blades 56 may be provided, disposed diametrically opposite with respect to the longitudinal center axis x-x of the inhaler 1. The freely extending rotor blades 56 protruding from the base or the top 23 of the rotary part 22 on the storage chamber side are positioned diametrically opposite in such a way that they are sufficiently spaced apart in the circumferential direction. Geometrically, they may substantially take up a quarter sector of the circular cross-section of the storage chamber 11.

In interaction with the plunger slide 25 fashioned as a flat part, the way in which the rotor blades 56 are disposed always achieves a surrounding region where the substance has been loosened. Furthermore, the way in which the dosing chamber 26 is disposed eccentrically in relation to the axis of rotation of the plunger slide 25 achieves optimum filling of the same by means of plunging helically through the mass of substance.

The co-rotation between the mouthpiece 3 and the closure cap 4, lifting off by an unscrewing action, takes place by a claw coupling 57 between the two. This comprises a longitudinal toothing 58 on the lateral wall 34 of the mouthpiece 3, which longitudinal toothing 58 engages in corresponding tooth gaps 59 on the inner side of the closure cap 4.

As the closure cap 4 is lifted off by an unscrewing action, the claw coupling 57 causes a co-rotation of the rotary part 22 and of the parts entrained by it, such as the sealing bush 50, the closure plug 52 and the plunger slide 25, an axial displacement of the plunger slide 25, brought about by the screw-effected lifting-off displacement of the closure cap 4, being in addition effected by the docking point 28, this axial displacement bringing about a screw-thread-like displacement of the dosing chamber 26 to the transfer point U, that is to say into the ready-to-transfer position according to the illustration in FIG. 4.

In the course of the linear displacement of the plunger slide 25, the closure plug 52 remains in its sealing position, supporting itself on the top 23 of the rotary part 22.

The standing spigot 20 rooted at the base 15 of the housing 2 is closed at the end by a screen-like cover 60. In the delimited space created as a result, a moisture-absorbing material 61 is held.

The plunger slide 25 can be varied with respect to the volume of its dosing chamber 26. All that is necessary for this is to exchange the key component of the dosing device D, that is the plunger slide 25, to achieve a different, precisely reproducible dosing of portions 10'.

The pressure-exerting base 13, acting in the manner of a plunger, is not impaired in its ability to move with respect to the cylinder space, which is provided by the central portion of the housing 2, since there the housing has an air-equalizing opening 62 lying to the rear of the annular lip 19.

The cup-shaped pressure-exerting base 13 has a central indentation, directed away from the storage chamber 11. It is of such a depth on the inside that the end portion of the plunger slide 25 projecting axially downward beyond the rotor blades 56 in the basic position is accommodated in it.

All features disclosed are (in themselves) pertinent to the invention. The disclosure content of the associated/accompanying priority documents (copy of the prior patent application) is also hereby incorporated in full in the disclosure of the application, including for the purpose of incorporating features of these documents in claims of the present application.

The invention claimed is:

1. An inhaler for powdered substances, comprising:
    a mouthpiece and a suction air channel leading to said mouthpiece;
    a storage chamber for storing therein the powdered substance;
    a flat-part plunger slide disposed to be linearly movable relative to said storage chamber and rotatable about a rotary axis; and
    said plunger slide having a dosing chamber formed therein eccentrically of said rotary axis, said dosing chamber being a transverse bore for apportioning a specific amount of the substance from said storage chamber and bringing the specific amount of the substance into a closed transfer position for transfer to a suction air stream through said suction air channel after opening the closed transfer position with the suction air stream; and
    a closure plunger having an opening formed therein for accepting said plunger slide, said closure plunger being movably disposed relative to said plunger slide, for closing off said dosing chamber outside said storage chamber.

2. The inhaler according to claim 1, wherein said closure plunger is moved along the rotary axis into a release position to open said dosing chamber by a suction vacuum.

3. The inhaler according to claim 2, wherein said closure plunger can be moved into a release position with respect to the dosing chamber in dependence on a reduced suction pressure.

4. The inhaler according to claim 1, wherein said suction air channel deflects in a radially outward direction above said dosing chamber.

5. The inhaler according to claim 4, wherein said plunger slide is formed with a radial collar forming a part of the flow deflection in the radially outward direction.

6. The inhaler according to claim 1, wherein said transverse bore is a conical transverse bore.

7. The inhaler according to claim 1, wherein said closure plunger is rotationally fixed with respect to said plunger slide.

* * * * *